US012800365B2

(12) United States Patent
Heusser

(10) Patent No.: US 12,800,365 B2
(45) Date of Patent: Nov. 17, 2026

(54) INLINE VISCOSITY MEASURING METHOD AND AN ASSOCIATED INLINE VISCOSITY MEASURING DEVICE

(71) Applicant: Promix Solutions AG, Winterthur (CH)

(72) Inventor: Rolf Heusser, Winterthur (CH)

(73) Assignee: Promix Solutions AG, Winterthur (CH)

( * ) Notice: Subject to any disclaimer, the term of this patent is extended or adjusted under 35 U.S.C. 154(b) by 224 days.

(21) Appl. No.: 18/930,691

(22) Filed: Oct. 29, 2024

(65) Prior Publication Data

US 2025/0146850 A1 May 8, 2025

(30) Foreign Application Priority Data

Nov. 7, 2023 (EP) .................................... 23208410
Sep. 26, 2024 (EP) .................................... 24203062

(51) Int. Cl.

*G01F 1/36* (2006.01)
*G01N 11/00* (2006.01)
*G01N 11/08* (2006.01)
*G01N 33/487* (2006.01)

(52) U.S. Cl.

CPC ............. *G01F 1/36* (2013.01); *G01N 33/487* (2013.01); *G01N 2011/0026* (2013.01); *G01N 2011/006* (2013.01); *G01N 11/08* (2013.01)

(58) Field of Classification Search

CPC .................... G01F 1/36; G01N 33/487; G01N 2011/0026; G01N 2011/006; G01N 11/08
USPC .......................................................... 73/54.01
See application file for complete search history.

(56) References Cited

U.S. PATENT DOCUMENTS 3,025,284 A * 3/1962 George ..................... C08F 4/12 526/197
3,712,875 A * 1/1973 Donatas ................. C08K 5/103 524/400
2003/0226405 A1 12/2003 Bell
2005/0178442 A1 8/2005 Halvorsen
2008/0134765 A1 6/2008 Baek
2023/0383058 A1* 11/2023 Jiang ...................... C08G 67/02

FOREIGN PATENT DOCUMENTS

CN 215262978 U 12/2021
DE 3306476 A1 8/1984
DE 4001341 A1 7/1991
FR 1228750 A 9/1960

OTHER PUBLICATIONS

European Search Report issued for European Application No. 23208410 on May 8, 2024, 2 pages.

* cited by examiner

*Primary Examiner* — Peter J Macchiarolo
*Assistant Examiner* — John M Royston
(74) *Attorney, Agent, or Firm* — Hard IP Professional Services LLC

(57) ABSTRACT

The invention relates to a method for measuring a pressure difference for determining a viscosity of a flowable medium and an associated device. The flowable medium flows through a measuring section arranged in a tubular element, in which at least one installation element is arranged, wherein an inlet pressure is measured at an inlet end of the tubular element and an outlet pressure is measured at an outlet end. A differential pressure between the inlet pressure and the outlet pressure is determined by means of a computer unit. The installation element is configured as at least one web element.

11 Claims, 3 Drawing Sheets

INLINE VISCOSITY MEASURING METHOD AND AN ASSOCIATED INLINE VISCOSITY MEASURING DEVICE

CROSS-REFERENCE TO RELATED APPLICATIONS

This application claims the benefit of European patent application no. EP 23208410.3, filed Nov. 7, 2023, and European patent application no. EP 24203062.5, filed Sep. 26, 2024, the contents of which are hereby incorporated by reference in their entirety.

BACKGROUND

The invention relates to an inline viscosity measuring method and an associated inline viscosity measuring device for measuring a pressure difference for determining the viscosity of a flowable medium. The invention relates in particular to the use of the method in a processing method for polyvinyl chloride (PVC), as well as a device for measuring a pressure difference for viscous liquids or slurries, for example for PVC, in particular a viscometer.

In a PVC processing method, the viscosity of the PVC melt is an interesting parameter that allows conclusions to be drawn about the raw material composition and the process parameters. It is therefore advantageous to measure the viscosity continuously and during the process. The continuous measurement of viscosity makes it possible to intervene during the manufacturing process in order to adjust the raw material composition or process parameters if necessary.

PVC is generally manufactured using an extrusion method. PVC is usually used as a solid in powder form or as granules as the starting material for the extrusion method. The PVC powder or PVC granulate is fed into the extruder and partially melted into a PVC melt with the addition of heat. The PVC melt that leaves the extruder is fed to a shaping tool in which the PVC melt is shaped into the desired product. The product that leaves the shaping tool is then cooled until the PVC melt solidifies. Such a product can be, for example, a film, a profile, a pipe element, a cable or even a granulate.

STATE OF THE ART

With PVC, so-called wall slip occurs in the flowable state. Wall slip is a rheological phenomenon that is only observed in a small number of polymers, including PVC. Under certain process conditions, a thin layer is formed in the PVC melt near a channel wall of a channel through which the PVC melt flows, which has a lower viscosity than the PVC melt outside the thin layer, i.e. in particular the PVC melt flowing at a greater distance from the channel wall. The wall friction can be reduced by the lower viscosity of the thin layer. Therefore, a measuring device, as described for example in US2005/0178442 A1, which carries out a measurement in the thin layer, can determine an incorrect value for the viscosity due to the wall friction of the channel wall. This measuring device thus determines the viscosity of the thin layer, consequently, the measured value is strongly influenced by the thin layer. Such a measurement is therefore not representative of the viscosity of the PVC melt outside the thin layer. Measuring devices attached to the channel wall or measuring devices using a constriction of a channel for measurement, such as a capillary according to DE 40 01 341 A1, or such as orifices, determine a pressure loss via the wall friction of the channel wall. Due to wall slip, the measured pressure loss is too low and therefore the determined viscosity is too low.

For these reasons, no reliable and reproducible viscosity measurement values can be generated with commercially available inline viscosity measuring devices for PVC melts and similar free-flowing media in which wall slip occurs. Measuring the pressure loss via an orifice plate is therefore not suitable for determining the viscosity of PVC melts, as the wall slip properties prevent a reproducible and meaningful measurement of the pressure loss. The pressure loss provides the basic parameter for determining the viscosity. However, a non-reproducible basic parameter cannot be used to determine a satisfactory measured value for the viscosity in practice. Since wall slip also depends on various factors, such as raw material composition, process temperature and shear behavior, the viscosity measured using a conventional orifice cannot simply be corrected with a factor.

In addition, PVC is not usually processed as a pure PVC melt. Depending on the degree of gelation, the PVC melt may contain solids that have not yet melted, which also influence the viscosity. When measuring the pressure loss via an orifice, the influence of the solids on the viscosity is not recorded, as the wall slip overlays the measurement. Without wall slip, the composition of the melt at or near the channel wall would be the same as in the inner area of the melt, so that the non-melted solids would have an effect on the measurement result and a correct measurement result corresponding to the composition of the melt would therefore be available. The inner area refers to the area of the melt having sufficient distance from the channel wall. For these reasons, it is not possible to calculate representative and reproducible viscosities using conventional pressure loss measurements via orifices and pipe constrictions.

Another challenge when processing PVC is the high risk of product decomposition. Conventional inline viscometers with a bypass, as shown for example in document DE 3306476, or the use of a melt pump require the PVC melt to remain in these measuring devices for too long, which leads to its decomposition and can therefore also lead to misleading measurement results.

Due to the wall slip properties, the friction between the channel wall and the PVC melt can change abruptly depending on the process conditions, in particular the friction can decrease abruptly. It has therefore been found that reproducible measurement results cannot be generated with conventional inline viscometers for PVC melts, in particular melts containing rigid PVC, especially with inline viscometers that contain orifices or channel constrictions via which the pressure loss is measured, and the viscosity is calculated on this basis.

According to CN215262978U, a viscosity coefficient measuring device including a resistance measuring tube is proposed. The resistance measuring tube includes a flow stabilizing device on the left and right sides of the resistance measuring tube and a resistance measuring device arranged at the top center, which is formed as a thin rod having a spherical end. The thin rod is attached to the upper inner wall of the resistance measuring tube and protrudes into the viscous fluid flowing through the resistance measuring tube. The thin rod with the spherical end is deflected by the fluid. The deflection is measured by the resistance measuring device. In addition, the pressure difference is measured via two secondary lines connected to the resistance measuring tube, which are arranged downstream and upstream of the resistance measuring device. The resistance measuring device and the thin rod with the spherical end are then removed to determine the pipe resistance coefficient. This measuring device is not suitable for in-line measurement, as the required interruption of the measuring activity would mean that no corresponding viscosity data would be available for a batch that would be processed during the interruption of the measuring activity.

SUMMARY OF THE INVENTION

The object of the invention is to develop a reliable and cost-effective method for measuring pressure differences of free-flowing media that tend to exhibit wall slip, in particular PVC melts, directly in the manufacturing process, i.e. inline, for example to determine a viscosity.

In particular, it is the object of the invention to measure the viscosity of rigid PVC in its processing method, such as an extrusion process, inline, continuously, reliably and cost-effectively.

When the term "for example" is used in the following description, this term refers to examples of embodiments and/or variants, which is not necessarily to be understood as a preferred application of the teaching of the invention. Similarly, the terms "preferably", "preferred" are to be understood as referring to an example from a set of embodiments and/or variants which is not necessarily to be understood as a preferred application of the teaching of the invention. Accordingly, the terms "for example", "preferably" or "preferred" may refer to a plurality of examples of embodiments and/or variants.

The following detailed description contains various embodiments of the inline viscosity measuring method according to the invention and the inline viscosity measuring device according to the invention. The description of a particular method or device is to be regarded as exemplary only. In the description and claims, the terms "containing", "comprising", "including" are interpreted as "comprising, but not limited to".

An inline viscosity measuring method for measuring a pressure difference to determine the viscosity of a flowable medium comprises the following steps: the flowable medium flows through a measuring section arranged in a tubular element, wherein the measuring section is configured as a flow channel, wherein the tubular element comprises a longitudinal axis, an inlet end and an outlet end. The measuring section extends between the inlet end and the outlet end. At least one installation element is arranged in the measuring section. An inlet pressure is measured at the inlet end by an inlet pressure sensor so that a measured inlet pressure value is obtained, and an outlet pressure is measured at the outlet end so that a measured outlet pressure value is obtained. According to an embodiment, the outlet pressure is determined by means of an outlet pressure sensor. Alternatively, the ambient pressure can also be used as the outlet pressure. According to this embodiment, the measuring section extends to the outlet end of a shaping tool, which is arranged downstream of the tubular element. The inlet pressure measurement value and the outlet pressure measurement value are converted by means of a transducer into measured variables that can be processed by a computer unit. The computer unit determines a differential pressure between the inlet pressure measured value and the outlet pressure measured value. The installation element is configured as at least one web element, with the web element projecting into the flow channel with a web element length LS which is at least 25% of a diameter DS of the flow channel.

In particular, the web element has a web element width that is a maximum of 30% of the web element length LS. The web element thus protrudes like a finger into the flowable medium flowing in the flow channel.

According to an embodiment, the web element has a first web element end and a second web element end, wherein neither the first web element end nor the second web element end is connected to the tubular element. In particular, both the first web element end and the second web element end are arranged in a distance from an inner wall of the tubular element which corresponds to at least 10% of the internal diameter of the tubular element. According to an embodiment, the web element includes a web element arm which is configured as a connecting element with the inner wall of the tubular element.

According to an embodiment, at least 60% of the cross-sectional area of the tubular element is covered by the web element or the web elements. In particular, at least 60% of the cross-sectional area and at most 90% of the cross-sectional area of the tubular element are covered by the web element or the web elements. In particular, at least two web elements can be provided. If two or more web elements are provided, they can be connected to each other.

A measured flow rate value of the flowable medium flowing through the tubular element can be determined, for example, by means of a flow rate sensor or a measured value correlated with the flow rate can be determined, for example, via the speed of a screw element of an extruder. A temperature sensor can determine a measured temperature value of the flowable medium flowing through the tubular element. The computer unit can determine a viscosity from the differential pressure and a measured flow rate value. According to an embodiment, the installation element is configured as at least one group of web elements. The group of web elements preferably contains a plurality of web elements.

According to an embodiment, the group of web elements contains at least two web elements. According to an embodiment, the group of web elements contains at least four web elements. The web elements of the group of web elements can be characterized in that they are arranged parallel to one another. In particular, the web elements extend from an inner wall of the tubular element into the interior of the tubular element. The length of the web elements is in particular at least a quarter, preferably at least a third of the internal diameter of the tubular element. The internal diameter of the tubular element corresponds to the diameter DS of the flow channel. The internal diameter of a non-circular tubular element is determined as the equivalent internal diameter according to the calculation rule given below. The calculation rule also applies analogously to the diameter DS of the flow channel.

It has been shown that the pressure loss as a basis for determining the viscosity can be measured in a reproducible and meaningful way using such web elements that engage in the flowable medium. It has been shown that wall slip doesn't occur with the intervening web elements or at least has no disturbing influence on the measurement result and that reproducible pressure losses can be measured, which can be used as a basis for determining the viscosity.

If the flowable medium contains solids, influences caused by these solids can also be recorded.

The web elements can extend in a first group plane and a second group plane, wherein the first group plane includes a first angle with the longitudinal axis of the tubular element and the second group plane includes a second angle with the longitudinal axis of the tubular element. According to a method variant, each of the group planes can contain at least two web elements. The web elements of each of the group planes can be characterized in that they are arranged parallel to one another. According to a method variant, the first group plane intersects with the second group plane.

According to a method variant, at least one of the first angle and the second angle measured in relation to the longitudinal axis has a value not equal to 90 degrees. In order to minimize the disruptive wall slip properties, web elements are used that are mounted at an angle not equal to 90 degrees with respect to the direction of flow. The direction of flow corresponds to the longitudinal axis of the tubular element.

According to a method variant, the first group plane and the second group plane each contain at least one web element. According to a method variant, at least one of the first and the second group planes contain at least two web elements. In particular, each of the first and second group planes contains at least two web elements. According to a variant of the method, a plurality of groups of web elements are arranged one behind the other in the measuring section.

According to a variant of the method, the tubular element has an internal diameter, with at least one of the web elements having a web element length LS that is greater than the internal diameter. According to a method variant, the web element length LS is a maximum of three times the internal diameter of the tubular element. It has also been shown that the web elements are fitted in a tubular section that is shorter than three times the internal diameter of the tubular element. Surprisingly, this arrangement avoids degradation of the PVC and keeps the additional pressure loss low.

An inline viscosity measuring method according to one of the preceding embodiments can be used, for example, in a processing method for PVC. Such a processing method for PVC can comprise an extruder, wherein the PVC is plasticized by means of the extruder.

According to an embodiment, the extruder contains a counter-rotating twin screw. In particular, the twin screw can comprise a first and a second screw element. The first screw element can be arranged parallel to the second screw element. The first and second screw elements can be arranged conically to one another. According to an embodiment, the twin screw has a first twin screw end and a second twin screw end, wherein the flowable medium emerges from the extruder at the second twin screw end.

According to an embodiment, a transition piece is arranged between the second twin-screw end and the inlet end of the tubular element. The transition piece can be used to change the channel cross-section. For example, the size of the cross-sectional area can be changed. For example, the transition piece can have a transition piece inlet end, and a transition piece outlet end with a corresponding cross-sectional area, whereby the cross-sectional area at the transition piece inlet end differs from the cross-sectional area at the transition piece outlet end. For example, the cross-sectional area at the transition piece inlet end can be larger than at the transition piece outlet end. Alternatively, the cross-sectional area at the transition piece inlet end can be smaller than at the transition piece outlet end. According to an embodiment, the shape of the cross-sectional area is changed, for example a circular cross-sectional area is converted into an oval or polygonal cross-sectional area or vice versa. The duct geometry can therefore be changed using the transition piece. There can be a maximum distance of four times the internal diameter of the tubular element between the second transition piece inlet end and the inlet end of the tubular element.

The cross-sectional area of the tubular element can be round, for example circular or oval, or have any polygonal shape, for example square, rectangular, pentagonal, hexagonal or octagonal. In addition, the tubular element containing the measuring section should preferably be attached directly after an extruder, as this provides ideal inlet flow conditions from the discharge screw into the tubular element, which has a positive effect on the prevention or neutralization of wall slip properties. The geometry of the web elements can have any shape. In particular, the web elements can have cross-sectional areas of any shape, for example the web elements can have a round cross-sectional area, for example a circular or oval cross-sectional area. Alternatively, the web elements can have any polygonal cross-sectional area, for example a square, rectangular, pentagonal, hexagonal or octagonal cross-sectional area. Web elements with different cross-sectional areas can be used in any combination.

An inline viscosity measuring device according to the invention for measuring a pressure difference to determine the viscosity of a flowable medium contains a measuring section arranged in a tubular element, which is configured for the flow of the flowable medium. The measuring section is configured as a flow channel. The tubular element has a longitudinal axis, an inlet end and an outlet end. The measuring section extends between the inlet end and the outlet end, wherein at least one installation element is arranged in the measuring section. An inlet pressure sensor for measuring an inlet pressure value is arranged at the inlet end. An outlet pressure can be measured at the outlet end so that a measured outlet pressure value is available. An outlet pressure sensor can be arranged at the outlet end to measure an outlet pressure value. Alternatively, an ambient pressure can be determined as the measured outlet pressure value. The inline viscosity measuring device can contain a transducer for converting the inlet pressure measured value and the outlet pressure measured value into measured variables that can be processed by a computer unit. A differential pressure between the measured inlet pressure value and the measured outlet pressure value can be determined from the measured variables by means of the computer unit. The installation element is configured as at least one web element, wherein the web element projects into the flow channel with a web element length LS which corresponds to at least 25% of a diameter DS of the flow channel.

According to an embodiment, the inline viscosity measuring device contains a flow sensor and a temperature sensor, whereby a measured flow value of the flowable medium flowing through the tubular element can be determined by means of the flow sensor, whereby a measured temperature value of the flowable medium flowing through the tubular element can be determined by means of the temperature sensor. Instead of a flow sensor, a measured value correlated with the flow rate can be determined via the speed of a screw element of an extruder. A temperature sensor can determine a measured temperature value of the flowable medium flowing through the tubular element. According to this embodiment, a viscosity can be determined from the differential pressure, the measured temperature value and the measured volume flow rate value by means of the computer unit.

According to an embodiment, the installation element is configured as at least one group of web elements, wherein the group of web elements preferably contains a plurality of web elements, but can also contain a single web element if, for example, the diameter of the flow channel is small.

According to an embodiment, the group of web elements contains at least two web elements. According to an embodiment, the group of web elements contains at least four web elements. The web elements of the group of web elements can be characterized in that they are arranged parallel to one another. In particular, the web elements extend from an inner wall of the tubular element into the interior of the tubular element. The length of the web elements is in particular at least a quarter, preferably at least a third of the internal diameter of the tubular element. The internal diameter of the tubular element corresponds to the diameter DS of the flow channel. The internal diameter of a non-circular tubular element is determined as the equivalent internal diameter according to the calculation rule given below. The calculation rule also applies analogously to the diameter DS of the flow channel.

It has been shown that using the inline viscosity measuring device according to the invention, the pressure loss can be measured reproducibly and meaningfully as a basis for determining the viscosity using such web elements that engage in the flowable medium. It has been shown that wall slip does not occur with the intervening web elements and that reproducible pressure losses can be measured, which can be used as a basis for determining the viscosity.

If the flowable medium contains solids, influences caused by these solids can also be recorded.

According to an embodiment, the web elements extend in a first group plane and a second group plane, wherein the first group plane includes a first angle to the longitudinal axis of the tubular element and the second group plane includes a second angle to the longitudinal axis of the tubular element. This arrangement has proven to be particularly advantageous in terms of measurement stability, especially if at least a portion of the web elements are connected to the tubular element in such a way that at least a portion of the web element ends are not connected to the tubular element.

According to an embodiment, the first group plane and the second group plane each contain at least one web element. According to an embodiment, each of the group planes can contain at least two web elements. The web elements of each of the group planes can be characterized in that they are arranged parallel to one another.

According to an embodiment, the first group plane intersects with the second group plane.

According to an embodiment, at least one of the first angles and the second angle measured in relation to the longitudinal axis has a value not equal to 90 degrees. In order to minimize the disruptive wall slip properties, web elements are used that are mounted at an angle not equal to 90 degrees to the direction of flow. The direction of flow corresponds to the longitudinal axis of the tubular element.

According to an embodiment, the first group plane and the second group plane each contain at least one web element.

According to an embodiment, at least one of the first and second group planes contains at least two web elements. In particular, each of the first and second group planes contains at least two web elements.

According to an embodiment, a plurality of groups of web elements are arranged one behind the other in the measuring section.

According to an embodiment, the tubular element has an internal diameter, with at least one of the web elements having a web element length LS that is greater than the internal diameter.

According to an embodiment, the web element length LS is a maximum of three times the internal diameter. It has also been shown that it is advantageous if the web elements are fitted in a tubular section that is shorter than three times the internal diameter of the tubular element. Surprisingly, this arrangement can prevent degradation of the PVC and keep the additional pressure loss low.

According to an embodiment, at least a portion of the web elements is connected to the tubular element in such a way that at least a portion of the web element ends is not connected to the tubular element. In other words, the tubular element can be regarded as a housing for the web elements. At least a part of the web elements is thus attached to the housing in such a way that the web element ends are at least partially not connected to the housing. For example, the web element can be connected to the tubular element via a web element arm. If several web elements are provided, the web elements can be connected to the tubular element via a common web element arm. Alternatively, a separate web element arm can be provided for each of the web elements, by means of which it is connected to the tubular element. It is also possible that the web elements of a first group of web elements and the web elements of a second group of web elements are connected to the tubular element by at least one common web element arm. In particular, the common web element arm can run in the intersection area when a first group plane with web elements intersects with a second group plane with web elements. A particularly good measurement stability is achievable if at least some of the web element ends are not connected to the tubular element.

An inline viscosity measuring device according to one of the preceding embodiments can, for example, be used in a processing method for PVC. Such a processing process for PVC may comprise an extruder, wherein the PVC is plasticized by means of the extruder.

According to an embodiment, the extruder includes a twin screw. In particular, the twin screw can comprise a first and a second screw element, wherein the first screw element is arranged parallel to the second screw element. Alternatively, the first screw element and the second screw element can be arranged conically to one another.

According to an embodiment, the twin screw has a first twin screw end and a second twin screw end, wherein the flowable medium emerges from the extruder at the second twin screw end. A distance of at most four times the internal diameter of the tubular element can be provided between the second twin screw end and the inlet end of the tubular element.

The web elements extend in particular from the inner wall of the tubular element into a central area of the tubular element. In particular, the central area is understood to be an area that contains the center axis of the tubular element. In particular, the central area comprises an area that is configured as a cylindrical area with a central area diameter. The diameter of the central area is at most half the internal diameter of the tubular element, with the center axis of the central area coinciding with the center axis of the tubular element.

In particular, the web elements are arranged in such a way that the flowable medium flowing through the tubular element can be divided into several partial flows, whereby the entire free cross-sectional area of the tubular element can be utilized by the partial flows. The free cross-sectional area refers to the proportion of the cross-sectional area that is available for the flowable medium. The free cross-sectional area does not contain any web elements and results from the difference between the cross-sectional area of the tubular element minus the cross-sectional area of the web elements. According to the invention, the flowable medium thus flows through the tubular element, particularly in the central area.

Using a tubular element according to the invention, it is thus possible for layers to be formed in the flowable medium. These layers can be rearranged by means of the web elements. The rearrangement of the layers leads to an avoidance of the wall slip properties.

According to an embodiment, the tubular element contains at least one web element. According to an embodiment, the at least one web element extends in the interior of the tubular element. In particular, a group can be formed as a plurality of web elements, wherein the plurality of web elements extend in the interior of the tubular element. According to an embodiment, at least a portion of the web elements are arranged crosswise to another portion of the web elements.

According to an embodiment, at least some of the web elements are connected to a housing which forms the tubular element.

The cross-sectional area of the tubular element can be round, for example circular or oval, or have any polygonal shape, for example square, rectangular, pentagonal, hexagonal or octagonal. If the cross-sectional area has a polygonal shape, the average diameter of the same can be determined from the cross-sectional area using the formula for the area of a circle.

The installation element or each of the installation elements can in particular comprise a first group of web elements and a second group of web elements, wherein the first group of web elements extends along a common first group plane and the second group of web elements extends along a second common group plane. The group plane is characterized in that it contains the central axis of the web elements. At least some of the web elements thus extend along the entire internal diameter of the tubular element.

The internal diameter corresponds to an average diameter if the tubular element is configured as a circular pipe. The mean diameter for an angular tubular element is defined as its circumference/n, so it is an equivalent diameter.

The dimensions of a web element are determined by its length, width and thickness. The length of the web element is measured from the first end of the web element to the second end of the web element.

The width of the web element is measured essentially transverse to the direction of flow. This means that the width essentially extends in a plane that is normal, i.e. at an angle of 90 degrees, to the length of the web element and shows the cross-section of the web element. The cross-section of the web element is characterized by its width and its thickness. The length of at least the longest web element is at least 5 times as great as its width.

The width of the web element is advantageously 0.2 to 8 times its thickness. If the width of the web element is 0.5 times to 4 times as large as its thickness, this results in a particularly preferred range in which the influence of the wall slip properties is at a minimum. The width of the web element is defined as the normal distance extending from the first edge and the second edge of the web element on the upstream side. The width of the web element on the upstream side may differ from the width measured on the downstream side of the web element.

The edge is understood to be the edge of the web element around which the fluid flows and which extends essentially parallel to the length of the web element. The thickness of the web element can be variable. The minimum thickness is less than 75% and advantageously less than 50% below the maximum thickness. The variations can be caused, for example, by ribs, indentations, nubs, wedge-shaped webs or other unevenness.

The web element is characterized by the fact that flat surfaces or concave surfaces are present in the direction of flow, which provide a contact surface for the flowing fluid medium. These surfaces aligned in the direction of flow have the effect that an increased outflow resistance can arise compared to a web element that is configured as a tubular element with a circular cross-sectional area.

The transition from at least one of the first and second ends of the web element to the inner wall of the tubular element can, in particular, be configured to be fluid. The web elements and the tubular element can therefore consist of a single component, which is preferably manufactured by a casting process. In particular, curves can be provided at the edges in the transition area from the web element to the tubular element so that the flow of the castable material is not impaired during the manufacturing process of the tubular element for the device.

BRIEF DESCRIPTION OF THE DRAWINGS

In the following, the inline viscosity measuring device according to the invention is illustrated by means of some exemplary embodiments. It is shown in.

DETAILED DESCRIPTION

Figure 1A:
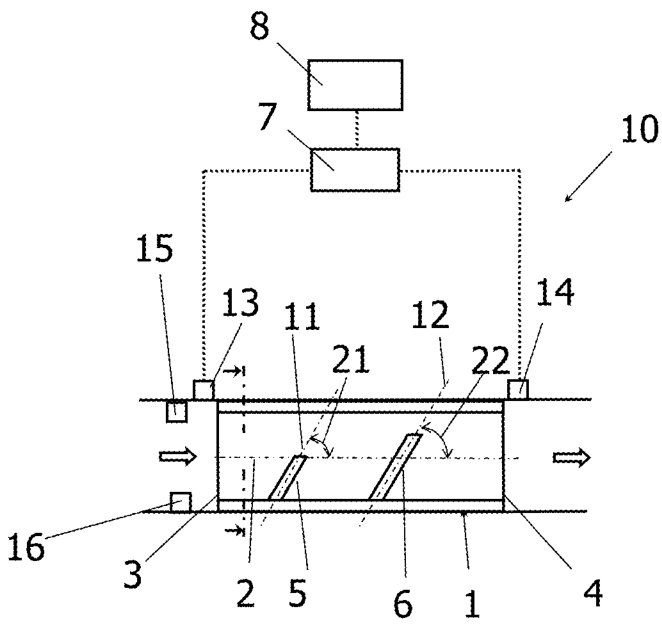
FIG. 1*a* a view of an inline viscosity measuring device according to a first embodiment, FIG. 1*b* a sectional view of the tubular element according to FIG. 1*a*, FIG. 2*a* a view of an inline viscosity measuring device according to a second embodiment, FIG. 2*b* a sectional view of the tubular element according to FIG. 2*a*, FIG. 3*a* a view of an inline viscosity measuring device according to a third embodiment, FIG. 3*b* a sectional view of the tubular element according to FIG. 3*a*, FIG. 4*a* a view of an inline viscosity measuring device according to a fourth embodiment, FIG. 4*b* a sectional view of the tubular element according to FIG. 4*a*, FIG. 5*a* a view of an inline viscosity measuring device according to a fifth embodiment, FIG. 5*b* a sectional view of the tubular element according to FIG. 5*a*, FIG. 6*a* a view of an inline viscosity measuring device according to a sixth embodiment, FIG. 6*b* a sectional view of the tubular element according to FIG. 6*a*.

FIG. 1*a* shows an inline viscosity measuring device 10 according to a first embodiment of the invention. The inline viscosity measuring device 10 for measuring a pressure difference to determine the viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, wherein at least one installation element 5, 6 is arranged in the measuring section. An inlet pressure sensor 13 for measuring an inlet pressure value is arranged at the inlet end 3. An outlet pressure sensor 14 for measuring an outlet pressure value is arranged at the outlet end 4. Alternatively, an ambient pressure can be determined at the outlet end. The device 10 contains a transducer 7 for converting the measured inlet pressure value and the measured outlet pressure value into measured variables that can be processed by a computer unit

8, so that a differential pressure between the measured inlet pressure value and the measured outlet pressure value can be determined from the measured variables by means of the computer unit 8. According to the present embodiment, the inline viscosity measuring device 10 also contains an optional flow sensor 15 and an optional temperature sensor 16, whereby the flow sensor 15 can be used to determine a measured flow value of the flowable medium flowing through the tubular element 1. By means of the temperature sensor 16, a measured temperature value of the flowable medium flowing through the tubular element 1 can be determined, whereby a viscosity can be determined from the differential pressure, the measured temperature value and the measured flow rate value by means of the computer unit 8. According to the present embodiment, a first installation element 5 and a second installation element 6 are provided. In particular, each of the installation elements 5, 6 is configured as at least one group of web elements.

The web elements of the installation element 5 extend in a first group plane 11. The web elements of the installation element 6 extend in a second group plane 12. The first group plane 11 includes a first angle 21 with the longitudinal axis of the tubular element. The second group plane 12 includes a second angle 22 with the longitudinal axis 2 of the tubular element 1. The first angle 21 can coincide with the second angle 22. According to an embodiment not shown, the first angle 21 may differ from the second angle 22.

The web elements of the first installation element 5 and the second installation element 6 extend from the inner wall of the tubular element 1 into the interior of the tubular element 1. According to the present embodiment, the web elements of the first installation element 5 have a length that differs from the web elements of the second installation element 6. According to the present exemplary embodiment, the web elements of the second installation element 6 are at least partially longer than the web elements of the first installation element 5. In the embodiment shown, the two web elements of the second installation element 6 are longer than the two web elements of the first installation element 5. According to an embodiment not shown, the web elements of the second installation element 6 are at least partially shorter than the web elements of the first installation element 5.

Of course, at least one of the first or second installation elements 5, 6 can contain more than two web elements, for example three, four, five, six, seven or eight web elements.

Of course, only a single installation element can also be provided, either a first installation element 5 or a second installation element 6 or an installation element that extends from the inner wall to the opposite inner wall, which is not shown in FIG. 1*a*.

Figure 1B:
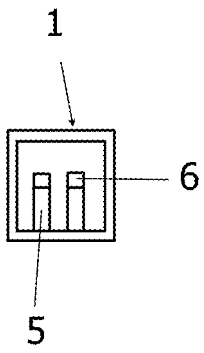

FIG. 1*b* shows a sectional view of the tubular element 1 according to FIG. 1*a*, which has been placed in the area of the inlet end 3, whereby the sectional plane is shown with a dotted line and arrows. The first installation element 5 is visible in the sectional view. The first installation element 5 comprises two web elements. The web elements of the first installation element 5 have central axes that lie in the first group plane 11. The second installation element 6 is arranged behind it and is therefore partially concealed by the first installation element 5 in this sectional view. The web elements of the second installation element 6 have central axes that lie in the second group plane 12.

According to the first embodiment shown in FIG. 1*a* and FIG. 1*b*, the first group plane 11 runs essentially parallel to the second group plane 12. In other words, the first angles 21 and the second angles 22 are the same if the tubular element 1 is formed without curvature. In other words, the longitudinal axis 2 of the tubular element 1 forms a straight line.

Figure 2A:
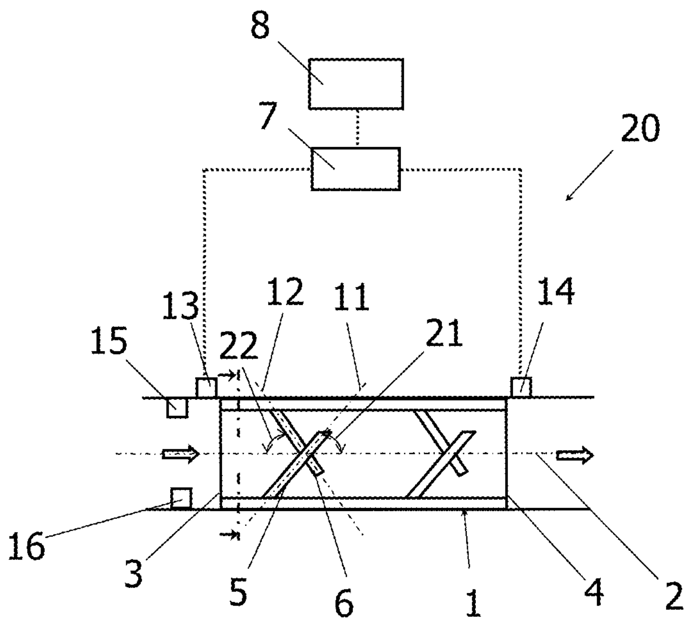

FIG. 2*a* shows an inline viscosity measuring device 20 according to a second embodiment of the invention. The same reference signs as in the first embodiment are used for components having the same effect. The inline viscosity measuring device 20 for measuring a pressure difference to determine the viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, wherein at least one installation element 5, 6 is arranged in the measuring section. According to the present embodiment, two arrangements of installation elements 5, 6 are arranged one behind the other.

An inlet pressure sensor 13 is arranged at the inlet end 3 to measure an inlet pressure value. An outlet pressure sensor 14 is arranged at the outlet end 4 to measure an outlet pressure value. Alternatively, an ambient pressure can be determined at the outlet end. The inline viscosity measuring device 20 contains a transducer 7 for converting the measured inlet pressure value and the measured outlet pressure value into measured variables that can be processed by a computer unit 8, so that a differential pressure between the measured inlet pressure value and the measured outlet pressure value can be determined from the measured variables by means of the computer unit 8. According to the present embodiment, the device 20 contains an optional flow sensor 15 and an optional temperature sensor 16, whereby the flow sensor 15 can be used to determine a measured volume flow value of the flowable medium flowing through the tubular element 1. By means of the temperature sensor 16, a measured temperature value of the flowable medium flowing through the tubular element 1 can be determined, whereby a viscosity can be determined from the differential pressure, the measured temperature value and the measured flow rate value by means of the computer unit 8.

According to this embodiment, each of the installation elements 5, 6 is formed as at least one group of web elements. The web elements, which form the first installation element 5, extend in a first group plane 11. The web elements, which form the second installation element 6, extend in a second group plane 12. The first group plane 11 includes a first angle 21 with the longitudinal axis of the tubular element 1. The second group plane 12 includes a second angle 22 with the longitudinal axis 2 of the tubular element 1. According to the present embodiment, the first group plane 11 intersects with the second group plane 12.

According to this embodiment, the first installation element 5 consists of a single web element. The web element of the first installation element 5 has a central axis that lies in the first group plane 11. The second installation element 6 is arranged behind it and is therefore partially concealed by the first installation element 5 in this sectional view. The web element of the second installation element 6 has a central axis that lies in the second group plane 12. The first group plane 11 intersects with the second group plane 12. In other words, the first and second installation elements 5, 6 intersect. The first and second installation elements 5, 6 have web elements which are connected to the inner wall of the pipe at only one end. In particular, the opposite end of the web elements is arranged at a distance from the opposite inner wall that is greater than the distance from the wall at which wall slip occurs. The opposite end is referred to below as the free end. In particular, the distance of the free end of at least one of the web elements can be at least one tenth of the internal diameter of the tubular element.

The web element of the first installation element 5 can differ in length from the web element of the second installation element 6.

FIG. 2*a* shows a first arrangement and a second arrangement. The first arrangement consists of the installation elements 5, 6. According to this embodiment, the second arrangement also consists of similar installation elements 5, 6, which are not labeled in FIG. 2*a* and are not visible in FIG. 2*b*, as they are covered by the installation elements 5, 6 of the upstream arrangement.

Figure 2B:
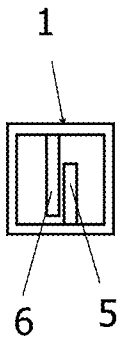

FIG. 2*b* shows a sectional view of the tubular element 1 according to FIG. 2*a*, which has been placed in the area of the inlet end 3, whereby the sectional plane is shown with a dotted line and arrows. The first installation element 5 and the second installation element 6 of the first arrangement are visible in the sectional view.

Figure 3A:
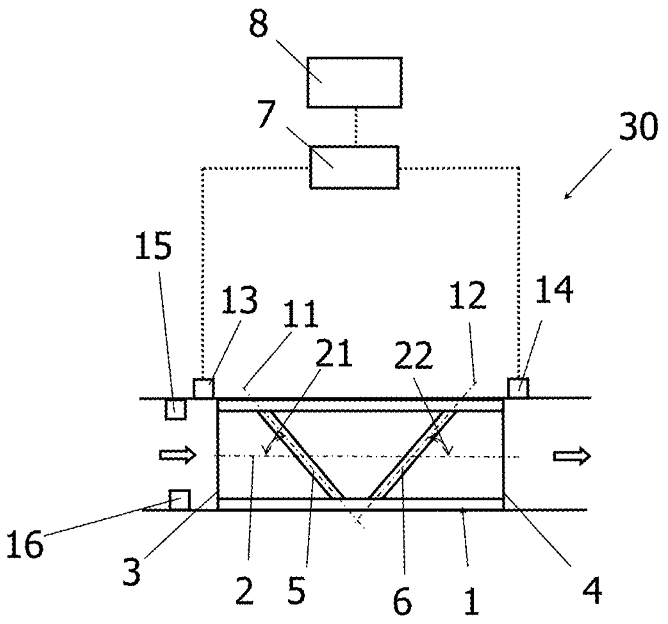

FIG. 3*a* shows an inline viscosity measuring device 30 according to a third embodiment of the invention. The inline viscosity measuring device 30 for measuring a pressure difference to determine the viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, wherein at least one installation element 5, 6 is arranged in the measuring section. An inlet pressure sensor 13 for measuring an inlet pressure value is arranged at the inlet end 3. An outlet pressure sensor 14 for measuring an outlet pressure value is arranged at the outlet end 4. Alternatively, an ambient pressure can be determined at the outlet end. The inline viscosity measuring device 30 contains a transducer 7 for converting the measured inlet pressure value and the measured outlet pressure value into measured variables that can be processed by a computer unit 8, so that a differential pressure between the measured inlet pressure value and the measured outlet pressure value can be determined from the measured variables by means of the computer unit 8. According to the present embodiment, the device 30 additionally contains an optional flow sensor 15 and an optional temperature sensor 16, whereby a flow measurement value of the flowable medium flowing through the tubular element 1 can be determined by means of the flow sensor 15. By means of the temperature sensor 16, a measured temperature value of the flowable medium flowing through the tubular element 1 can be determined, whereby a viscosity can be determined from the differential pressure, the measured temperature value and the measured flow value by means of the computer unit 8.

According to the present embodiment, a first installation element 5 and a second installation element 6 are provided. Each of the installation elements 5, 6 can be configured as at least one group of web elements which extend in a first group plane 11 and a second group plane 12. The first group plane 11 includes a first angle 21 with the longitudinal axis of the tubular element and the second group plane 12 includes a second angle 22 with the longitudinal axis 2 of the tubular element 1.

Figure 3B:
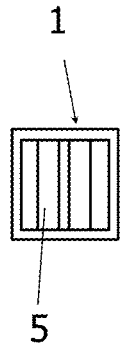

FIG. 3*b* shows a sectional view of the tubular element 1 according to FIG. 3*a*, which has been placed in the area of the inlet end 3. The first installation element 5 is visible in the sectional view. The second installation element 6 is located behind it and is therefore concealed by the first installation element 5 in this sectional view. According to the present embodiment, the first installation element 5 consists of two web elements.

Figure 4A:
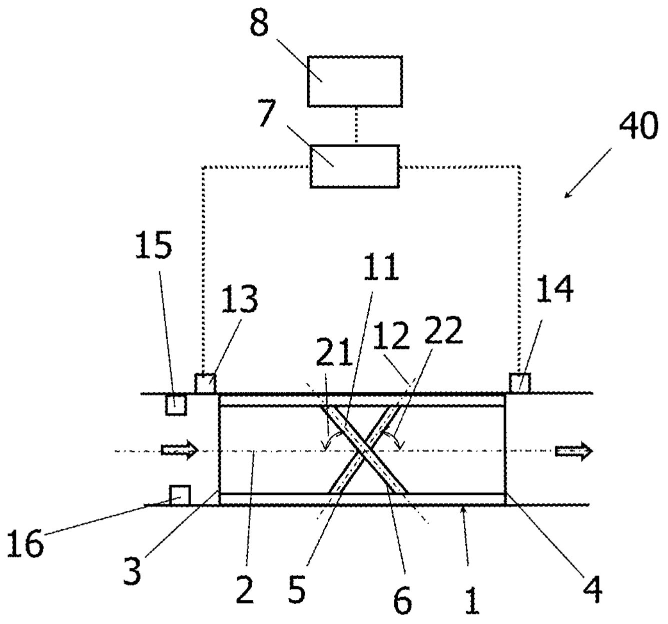

FIG. 4*a* shows an inline viscosity measuring device 40 according to a fourth embodiment of the invention. The same reference signs as in the first embodiment are used for components having the same effect. The inline viscosity measuring device 40 for measuring a pressure difference to determine a viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, whereby at least one installation element 5, 6 is arranged in the measuring section. An inlet pressure sensor 13 for measuring an inlet pressure value is arranged at the inlet end 3. An outlet pressure sensor 14 for measuring an outlet pressure value is arranged at the outlet end 4. Alternatively, an ambient pressure can be determined at the outlet end. The device 40 contains a transducer 7 for converting the measured inlet pressure value and the measured outlet pressure value into measured variables that can be processed by a computer unit 8, so that a differential pressure between the measured inlet pressure value and the measured outlet pressure value can be determined from the measured variables by means of the computer unit 8. According to the present embodiment, the device 40 additionally contains an optional flow sensor 15 and an optional temperature sensor 16, whereby a flow rate measurement value of the flowable medium flowing through the tubular element 1 can be determined by means of the flow sensor 15. By means of the temperature sensor 16, a measured temperature value of the flowable medium flowing through the tubular element 1 can be determined, whereby a viscosity can be determined from the differential pressure, the measured temperature value and the measured flow rate value by means of the computer unit 8.

The installation element 5, 6 is configured as at least one group of web elements which extend in a first group plane 11 and a second group plane 12, wherein the first group plane 11 includes a first angle 21 with the longitudinal axis of the tubular element and the second group plane 12 includes a second angle 22 with the longitudinal axis 2 of the tubular element 1. According to the present embodiment, the first group plane 11 intersects with the second group plane 12.

Figure 4B:
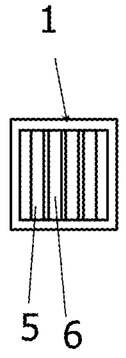

FIG. 4*b* shows a sectional view of the tubular element 1 according to FIG. 4*a*, which has been laid in the area of the inlet end 3. The first installation element 5 and the second installation element 6 are visible in the sectional view. According to this embodiment, the installation element 5 consists of two web elements and the installation element 6 consists of two web elements.

Figure 5A:
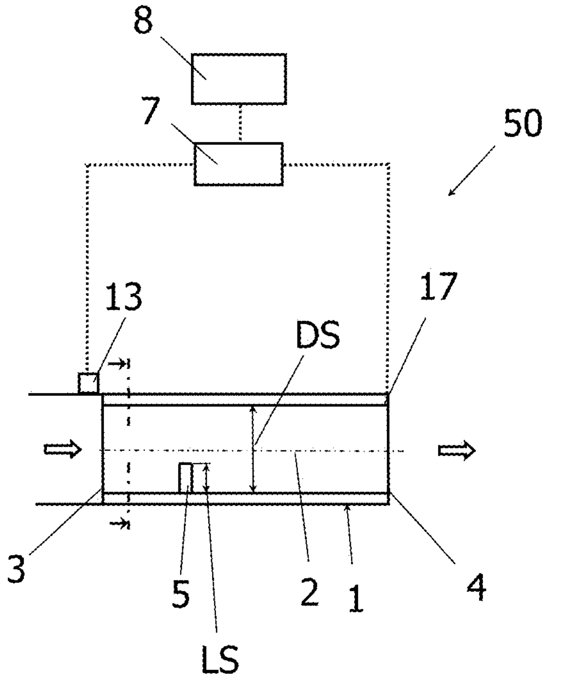

FIG. 5*a* shows an inline viscosity measuring device 50 according to a fifth embodiment of the invention. The inline viscosity measuring device 50 for measuring a pressure difference to determine a viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, whereby at least one installation element 5 is arranged in the measuring section. An inlet pressure sensor 13 for measuring an inlet pressure value is arranged at the inlet end 3. An outlet pressure measurement value 17 is determined at the outlet end 4. According to the present embodiment, an ambient pressure is determined at the outlet end. The inline viscosity measuring device 50 contains a transducer 7 for converting the measured inlet pressure value and the measured outlet pressure value into measured variables that can be processed by a computer unit 8, so that a differential pressure between the measured inlet pressure value and the measured outlet pressure value can be determined from the measured variables by means of the computer unit 8. The inline viscosity measuring device 50 can also include optionally at least one of a flow sensor and a temperature sensor. Alternatively, instead of a flow sensor, another transducer can be provided for the measured flow value. For example, the speed of a screw element of an extruder can be determined. The flow sensor or another sensor can be used to determine a measured flow value of the flowable medium flowing through the tubular element 1. By means of the optional temperature sensor, a measured temperature value of the flowable medium flowing through the tubular element 1 can be determined, whereby a viscosity can be determined from the differential pressure, possibly the measured temperature value and possibly the measured flow value by means of the computer unit 8.

According to the present embodiment, only a first installation element 5 is provided. In particular, the installation element 5 is configured as at least one web element. The web element protrudes into the flow channel with a web element length LS which is at least 25% of a diameter DS of the flow channel.

The web element or web elements of the first installation element 5 extend from the inner wall of the tubular element 1 into the interior of the tubular element 1 or the flow channel.

Of course, the installation element 5 can contain two web elements or more than two web elements, for example three, four, five, six, seven or eight web elements.

Figure 5B:
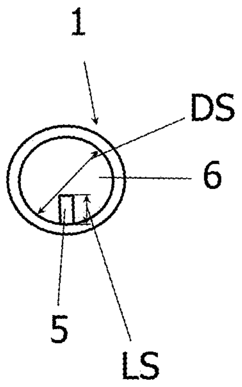

Of course, the installation element can extend from the inner wall to the opposite inner wall, which is not shown in FIG. 5*a* or FIG. 5*b*.

FIG. 5*b* shows a sectional view of the tubular element 1 according to FIG. 5*a*, which has been placed in the area of the inlet end 3, whereby the sectional plane is shown with a dotted line and arrows. The first installation element 5 is visible in the sectional view. According to this exemplary embodiment, the first installation element 5 consists of a single web element. The at least one web element of the installation element 5 can include an angle of 90 degrees in relation to the longitudinal axis 2, as shown in FIG. 5*a*. The angle can also deviate from 90 degrees, which is not shown in the drawing.

Figure 6A:
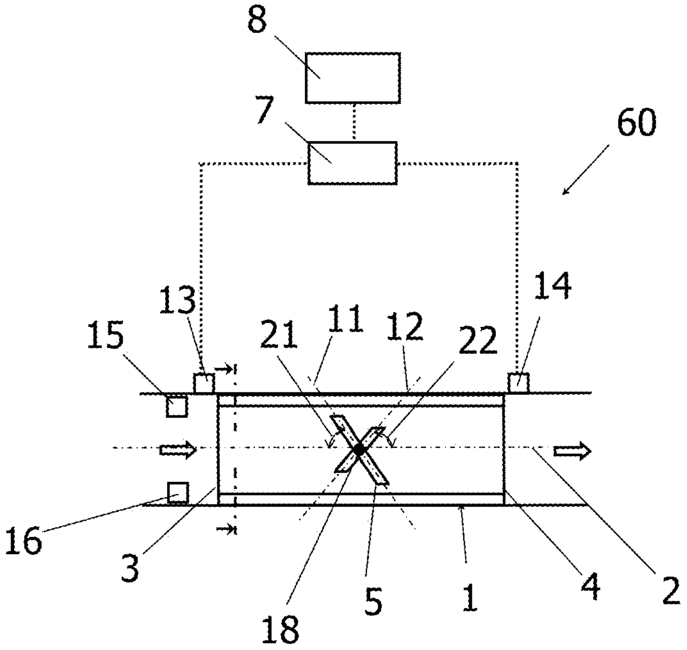

FIG. 6*a* shows an inline viscosity measuring device 60 according to a sixth embodiment of the invention. The inline viscosity measuring device 60 for measuring a pressure difference to determine a viscosity of a flowable medium contains a measuring section arranged in a tubular element 1, which is configured for the flow of the flowable medium. The measuring section is configured as a flow channel. The tubular element 1 comprises a longitudinal axis 2, an inlet end 3 and an outlet end 4. The measuring section extends between the inlet end 3 and the outlet end 4, wherein at least one installation element 5 is arranged in the measuring section. An inlet pressure sensor 13 for measuring an inlet pressure value is arranged at the inlet end 3. An outlet pressure sensor 14 for measuring an outlet pressure value is arranged at the outlet end 4. Alternatively, an ambient pressure can be determined at the outlet end, as shown in FIG. 5*a*. The inline viscosity measuring device 60 contains a converter 7 for converting the measured inlet pressure value and the measured outlet pressure value into measured variables that can be processed by a computer unit 8, so that a differential pressure between the measured inlet pressure value and the measured outlet pressure value can be determined from the measured variables by means of the computer unit 8. The inline viscosity measuring device 60 can also include an optional flow sensor 15 and/or an optional temperature sensor 16. Alternatively, instead of a flow sensor, another transducer can be provided for the measured flow value. For example, a rotational speed of a screw element of an extruder can be determined. The flow sensor or another sensor can be used to determine a measured flow value of the flowable medium flowing through the tubular element 1. By means of the optional temperature sensor, a measured temperature value of the flowable medium flowing through the tubular element 1 can be determined, whereby a viscosity can be determined from the differential pressure, possibly the measured temperature value and possibly the measured flow value by means of the computer unit 8.

According to the present embodiment, only a first installation element 5 is provided. In particular, the installation element 5 contains at least one web element. The web element protrudes into the flow channel with a web element length LS which is at least 25% of a diameter DS of the flow channel, see FIG. 6*b*.

The web element or web elements of the first installation element 5 extend from the center axis of the tubular element 1 into the interior of the tubular element 1 or the flow channel. According to the present embodiment, the web element or each of the web elements has a first web element end and a second web element end, with neither the first web element end nor the second web element end being connected to the tubular element. In particular, both the first web element end and the second web element end have a distance from an inner wall of the tubular element which corresponds to at least 10% of the internal diameter of the tubular element, or the diameter DS of the flow channel. According to an embodiment, the web element includes a web element arm 18, which is configured as a connecting element with the inner wall of the tubular element. In FIG. 6*a*, one of the two web element arms 18 is shown in section, as the front side wall of the tubular element 1 lies in front of the sectional plane and is therefore cut away in FIG. 6*a*.

According to an embodiment, at least 60% of the cross-sectional area of the tubular element is covered by the web element(s). In particular, at least 60% of the cross-sectional area and at most 90% of the cross-sectional area of the tubular element are covered by the web element or the web elements. In particular, at least two web elements can be provided. If two or more web elements are provided, they can be connected to each other via web element arms 18, as shown in FIG. 6*b*.

According to the present embodiment, the installation element 5 is formed as a group of web elements extending in a first group plane 11 and a second group plane 12, wherein the first group plane 11 includes a first angle 21 with the longitudinal axis of the tubular element and the second group plane 12 includes a second angle 22 with the longitudinal axis 2 of the tubular element 1. According to the present embodiment, the first group plane 11 intersects with the second group plane 12 and the installation element 5 can of course contain two web elements or more than two web elements, for example three, four, five, six, seven or eight web elements. Of course, the installation element can extend from the inner wall to the opposite inner wall, which is not shown in FIG. 6*a* or FIG. 6*b*.

Figure 6B:
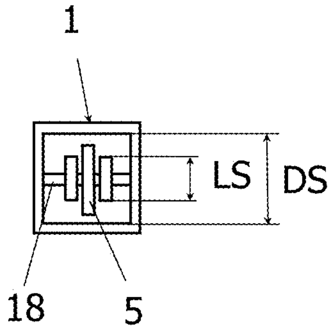

FIG. 6*b* shows a sectional view of the tubular element 1 according to FIG. 6*a*, which has been placed in the area of the inlet end 3, whereby the sectional plane is shown with a dotted line and arrows. The first installation element 5 is visible in the sectional view. According to this exemplary embodiment, the first installation element 5 consists of three web elements.

The web elements of the installation element 5 can include an angle of less or more than 90 degrees in relation to the longitudinal axis 2, as shown in FIG. 6*a*. The angle can also be 90 degrees, which is not shown in the drawing.

According to any of the embodiments, the web element or at least part of the web elements can extend over the entire internal diameter of the tubular element.

The internal diameter can correspond to an average diameter if the cross-section of the tubular element is not circular. The mean diameter corresponds to the internal diameter if the tubular element has a circular cross-sectional area. The mean diameter for an angular or oval tubular element is defined as its circumference/n, so it is an equivalent diameter.

The dimensions of a web element are determined by its length, width and thickness. The length of the web element is measured from the first end of the web element to the second end of the web element.

The width of the web element is measured essentially transverse to the direction of flow. This means that the width extends essentially in a plane that is normal to the length of the web element and shows the cross-section of the web element. The cross-section of the web element is characterized by its width and its thickness. The length of at least the longest web element is at least 5 times as great as its width.

The width of the web element is 0.5 to 5 times as large as its thickness, advantageously 0.5 to 3 times as large as its thickness. If the width of the web element is 0.5 to 2 times as large as its thickness, this results in a particularly preferred range in which the influence of the wall slip properties is at a minimum. The width of the web element is defined as the perpendicular distance extending from the first edge and the second edge of the web element on the upstream side. The width of the web element on the upstream side may differ from the width of the web element measured on the downstream side.

An edge is understood to be the edge of the web element around which the fluid flows and which extends essentially parallel to the length of the web element. The thickness of the web element can be variable. The minimum thickness is less than 75% and advantageously less than 50% below the maximum thickness. The variations can be caused, for example, by ribs, indentations, nubs, wedge-shaped webs or other profile variations or unevenness.

The web element is characterized by the fact that flat surfaces, convex surfaces or concave surfaces are present in the direction of flow, which provide a contact surface for the flowable medium. These surfaces aligned in the direction of flow have the effect that an increased outflow resistance can arise compared to a web element that is configured as a tubular element with a circular cross-sectional area.

The transition from at least one of the first and second ends of the web element to the inner wall of the tubular element can in particular be configured to be flowing. The web elements and the tubular element can therefore consist of a single component, which is preferably produced by a casting process. In particular, curves can be provided at the edges in the transition area from the web element to the tubular element so that the flow of the castable material is not impaired during the manufacturing process of the tubular element for the device.

It is obvious to a person skilled in the art that many other variants in addition to the described methods or devices are possible without deviating from the inventive concept. The subject matter of the invention is thus not limited by the preceding description and is determined by the scope of protection defined by the claims. For the interpretation of the claims or the description, the broadest possible reading of the claims is decisive. In particular, the terms "comprising" or "including" are to be interpreted as referring to elements, components or steps in a non-exclusive meaning, indicating that the elements, components or steps may be present or used, that they may be combined with other elements, components or steps not explicitly mentioned. When the claims refer to an element or component from a group which may comprise A, B, C to N elements or components, this formulation is to be interpreted as requiring only a single element of this group, and not a combination of A and N, B and N or any other combination of two or more elements or components of this group.

What is claimed is:

1. An inline viscosity measuring method for measuring a pressure difference for determining a viscosity of a flowable medium, wherein the flowable medium flows through a measuring section arranged in a tubular element, wherein the measuring section is configured as a flow channel, wherein the tubular element comprises a longitudinal axis, an inlet end and an outlet end, wherein the measuring section extends at least between the inlet end and the outlet end, wherein at least one installation element is arranged in the measuring section, wherein an inlet pressure at the inlet end is measured by an inlet pressure sensor, so that a measured inlet pressure value is obtained, and wherein an outlet pressure is measured at the outlet end so that a measured outlet pressure value is obtained, wherein the measured inlet pressure value and the measured outlet pressure value are converted by means of a transducer into measured variables which can be processed by a computer unit, wherein the computer unit determines a differential pressure between the measured inlet pressure value and the measured outlet pressure value, wherein the at least one installation element is configured as at least one web element, wherein the at least one web element projects into the flow channel with a web element length LS which corresponds to at least 25% of a diameter DS of the flow channel, wherein the flowable medium comprises polyvinyl chloride (PVC), wherein the PVC is plasticized by means of an extruder, wherein the extruder comprises a counter-rotating twin screw, wherein the counter-rotating twin screw has a first twin screw end and a second twin screw end, wherein the flowable medium emerges from the extruder at the second twin screw end, wherein a transition piece is arranged between the second twin screw end and the inlet end of the tubular element, wherein the transition piece has a transition piece inlet end with a corresponding transition piece inlet end cross-sectional area and a transition piece outlet end with a corresponding transition piece outlet end cross-sectional area, and wherein the corresponding transition piece inlet end cross-sectional area differs from the corresponding transition piece outlet end cross-sectional area.

2. The inline viscosity measuring method of claim 1, wherein a group of web elements extend in a first group plane and a second group plane, wherein the first group plane includes a first angle to the longitudinal axis of the tubular element and the second group plane includes a second angle to the longitudinal axis of the tubular element.

3. The inline viscosity measuring method of claim 2, wherein the first group plane intersects with the second group plane.

4. The inline viscosity measuring method of claim 2, wherein at least one of the first angle and the second angle measured with respect to the longitudinal axis has a value not equal to 90 degrees.

5. The inline viscosity measuring method of claim 2, wherein the first group plane and the second group plane each contain at least one corresponding web element.

6. The inline viscosity measuring method of claim 2, wherein a plurality of groups of web elements are arranged one behind another one in the measuring section.

7. The inline viscosity measuring method of claim 1, wherein the tubular element has an internal diameter, wherein at least one web element of a plurality of groups of web elements has the web element length LS which is greater than the internal diameter.

8. The inline viscosity measuring method of claim 1, wherein at least a part of the at least one web element is connected to the tubular element in such a way that at least a part of an end of the at least one web element is not connected to the tubular element.

9. An inline viscosity measuring device for measuring a pressure difference for determining a viscosity of a flowable medium, containing a measuring section which is arranged in a tubular element and which is configured for a flow of the flowable medium, wherein the measuring section is configured as a flow channel, wherein the tubular element comprises a longitudinal axis, an inlet end and an outlet end, wherein the measuring section extends at least between the inlet end and the outlet end, wherein at least one installation element is arranged in the measuring section, wherein an inlet pressure sensor for measuring a measured inlet pressure value is arranged at the inlet end, wherein an outlet pressure can be measured at the outlet end so that a measured outlet pressure value is obtainable, wherein the inline viscosity measuring device contains a transducer for converting the measured inlet pressure value and the measured outlet pressure value into measured variables which can be processed by a computer unit, so that a differential pressure between the measured inlet pressure value and the measured outlet pressure value can be determined from the measured variables by means of the computer unit, wherein the at least one installation element is configured as at least one web element, wherein the at least one web element projects into the flow channel with a web element length LS which corresponds to at least 25% of a diameter DS of the flow channel, wherein the flowable medium comprises polyvinyl chloride (PVC), wherein an extruder is provided for plasticizing the PVC from a granulate or powder, wherein the extruder comprises a counter-rotating twin screw, wherein the counter-rotating twin screw has a first twin screw end and a second twin screw end configured for discharge of the flowable medium from the extruder at the second twin screw end, wherein a transition piece is arranged between the second twin screw end and the inlet end of the tubular element, wherein the transition piece has a transition piece inlet end with a corresponding transition piece inlet end cross-sectional area and a transition piece outlet end with a corresponding transition piece outlet end cross-sectional area, and wherein the corresponding transition piece inlet end cross-sectional area differs from the corresponding transition piece outlet end cross-sectional area.

10. The inline viscosity measuring device of claim 9, wherein the at least one installation element is configured as at least one group of web elements, wherein the at least one group of web elements extend in a first group plane and in a second group plane, wherein the first group plane includes a first angle with the longitudinal axis of the tubular element and the second group plane includes a second angle with the longitudinal axis of the tubular element, wherein at least one of the first angle and the second angle measured with respect to the longitudinal axis has a value not equal to 90 degrees.

11. The inline viscosity measuring device of claim 9, wherein at least a part of the at least one web element is connected to the tubular element in such a way that at least a part of an end of the at least one web element is not connected to the tubular element.

* * * * *